(12) United States Patent
Adams

(10) Patent No.: US 12,336,672 B2
(45) Date of Patent: Jun. 24, 2025

(54) TOILET SEAT TRAP

(71) Applicant: Ophelia Denise Adams, Raleigh, NC (US)

(72) Inventor: Ophelia Denise Adams, Raleigh, NC (US)

( * ) Notice: Subject to any disclaimer, the term of this patent is extended or adjusted under 35 U.S.C. 154(b) by 39 days.

(21) Appl. No.: 18/335,219

(22) Filed: Jun. 15, 2023

(65) Prior Publication Data

US 2024/0215776 A1   Jul. 4, 2024

Related U.S. Application Data

(60) Provisional application No. 63/478,116, filed on Dec. 31, 2022.

(51) Int. Cl.
*A47K 13/16* (2006.01)
*A61B 10/00* (2006.01)

(52) U.S. Cl.
CPC .......... *A47K 13/16* (2013.01); *A61B 10/0038* (2013.01)

(58) Field of Classification Search
CPC ............................ A47K 13/16; A61B 10/0038
See application file for complete search history.

(56) References Cited

U.S. PATENT DOCUMENTS

| | | | | |
|---|---|---|---|---|
| 3,540,433 A * | 11/1970 | Brockman | ......... | A61B 10/0038 4/144.1 |
| 3,588,921 A * | 6/1971 | Nagel | ................ | A61B 10/0038 4/315 |
| 4,309,782 A * | 1/1982 | Paulin | ................ | A61B 10/0038 4/144.1 |
| 5,437,906 A | 8/1995 | Snuggs | | |
| 6,775,852 B1 * | 8/2004 | Alvarez | ............... | A61B 10/007 4/144.2 |
| 6,813,784 B1 * | 11/2004 | Thompson | ............. | A47K 13/16 4/245.4 |
| 6,851,131 B1 * | 2/2005 | Adams | ................... | A47K 13/14 4/245.7 |
| 6,968,578 B2 * | 11/2005 | Bernsley | ................ | A47K 13/06 4/245.3 |
| 7,247,360 B1 | 7/2007 | Besner et al. | | |
| 7,328,465 B1 | 2/2008 | Morad | | |
| 2013/0111656 A1 * | 5/2013 | Seibt | ..................... | A47K 13/165 4/245.4 |
| 2014/0329273 A1 * | 11/2014 | Fiedler | ............... | A61B 10/0038 435/309.1 |
| 2018/0317892 A1 * | 11/2018 | Catlin | ..................... | A47K 11/02 |
| 2019/0239862 A1 * | 8/2019 | Suehiro | .................. | G01N 33/48 |
| 2020/0129161 A1 * | 4/2020 | McNulty | ............ | A61B 10/0038 |

FOREIGN PATENT DOCUMENTS

CA    2919625    9/2015

* cited by examiner

*Primary Examiner* — Daniel L Cerioni
(74) *Attorney, Agent, or Firm* — Buchanan Ingersoll & Rooney PC

(57) ABSTRACT

The present invention provides a toilet seat cover to protect a user from both the toilet seat and the toilet bowl water with its associated contaminants. The toilet seat cover is made up of a) a sheet capable of covering a toilet seat b) a trap attached to the sheet, and c) a device, such as a drawstring or an elastic string, that can be located in a casing proximate an outer edge of the sheet and used to removably attach the toilet seat trap to the toilet seat. The trap provides an opening in the sheet and a barrier between the opening and a toilet bowl water when the toilet seat cover is removably attached to the toilet seat.

18 Claims, 3 Drawing Sheets

TOILET SEAT TRAP

CROSS-REFERENCE

This application claims priority under 35 U.S.C. 119(e) to U.S. Provisional Application Ser. No. 63/478,116 filed on Dec. 31, 2022, which is incorporated herein by reference in its entirety.

FIELD OF INVENTION

The present invention relates generally to an article that can improve sanitation for someone using a toilet. The present invention also relates to a specimen collector used in conjunction with an article that can improve sanitation.

BACKGROUND OF THE INVENTION

The cleanliness of public toilets and concerns about encountering contamination in the form or bacteria, viruses, or human waste have been an ongoing issue.

Toilet seat covers to date have focused on providing a barrier between a toilet seat user's skin and the toilet seat. The traditional toilet seat cover does not protect a user from contents within the toilet bowl. While using and/or flushing a toilet bowl, an aerosol of some toilet bowl water and germs/viruses, as well as splashes of toilet bowl water, can rise from the toilet bowl. There is a need for something analogous to the mask a person wore during the Covid virus epidemic to protect others from the aerosols leaving the mask wearer's mouth for use to protect people from the aerosols leaving the toilet bowl.

Traditional toilet seat covers provide a barrier between a toilet seat user's skin and the toilet seat. There is a need for an improved toilet seat cover that provides protection from the contents of the toilet bowl. There is also a need for a toilet seat cover that can be used to collect medical samples, e.g., kidney stone, stool sample, etc.

BRIEF SUMMARY OF THE INVENTION

According to an embodiment of the present invention, a toilet seat cover comprises a) a sheet capable of covering a toilet seat, b) a trap attached to the sheet and centrally located on the sheet, and c) a device capable of removably attaching the toilet seat cover to the toilet seat. The trap provides an opening in the sheet and a barrier between the opening and a toilet bowl water when the toilet seat cover is removably attached to the toilet seat.

According to another embodiment of the present invention, a toilet seat cover comprises a) a sheet capable of covering a toilet seat, b) a trap attached to the sheet and centrally located on the sheet, and c) a device capable of removably attaching the toilet seat cover to the toilet seat. The trap provides an opening in the sheet and a barrier between the opening and a toilet bowl water when the toilet seat cover is removably attached to the toilet seat. The toilet seat cover is water soluble and hypoallergenic. The sheet and the trap are made of non-woven fabric.

According to yet another embodiment of the present invention, a toilet seat cover comprises a) a sheet capable of covering a toilet seat, b) a trap attached to the sheet and centrally located on the sheet, c) a device capable of removably attaching the toilet seat cover to the toilet seat, and d) an optional specimen collector capable of being removably attached to the trap and useful for collecting medical samples. The trap provides an opening in the sheet and a barrier between the opening and a toilet bowl water when the toilet seat cover is removably attached to the toilet seat. The trap is cylindrical or bowl shaped and capable of receiving the biological specimen collector, and the bottom of the trap comprises thicker fabric than the rest of the trap and/or the sheet. The device is located in a casing proximate an outer edge of the sheet, and the device is selected from the group consisting of a drawstring or an elastic string. The sheet, the trap, and the device are water soluble.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

According to an embodiment of the present invention, a toilet seat cover comprises a) a sheet capable of covering a toilet seat, b) a trap attached to the sheet and centrally located on the sheet, and c) a device capable of removably attaching the toilet seat cover to the toilet seat. The trap provides an opening in the sheet and a barrier between the opening and a toilet bowl water when the toilet seat cover is removably attached to the toilet seat.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise.

As used herein, the term "and/or", when used in a list of two or more items, means that any one of the listed items can be employed by itself, or any combination of two or more of the listed items can be employed. For example, if a composition is described as containing compounds A, B, "and/or" C, the composition may contain A alone; B alone; C alone; A and B in combination; A and C in combination; B and C in combination; or A, B, and C in combination.

Figure 1:
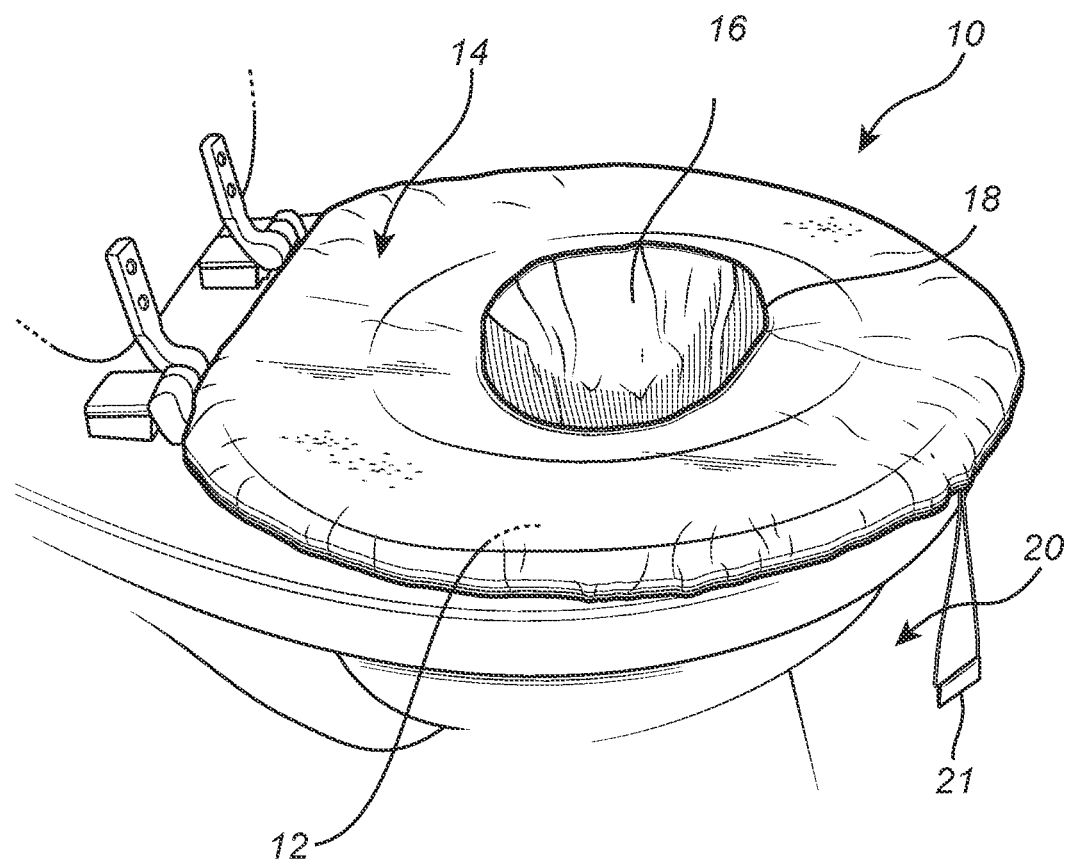
FIG. 1 is an isometric view of a non-limiting embodiment of the present invention.
Figure 2:
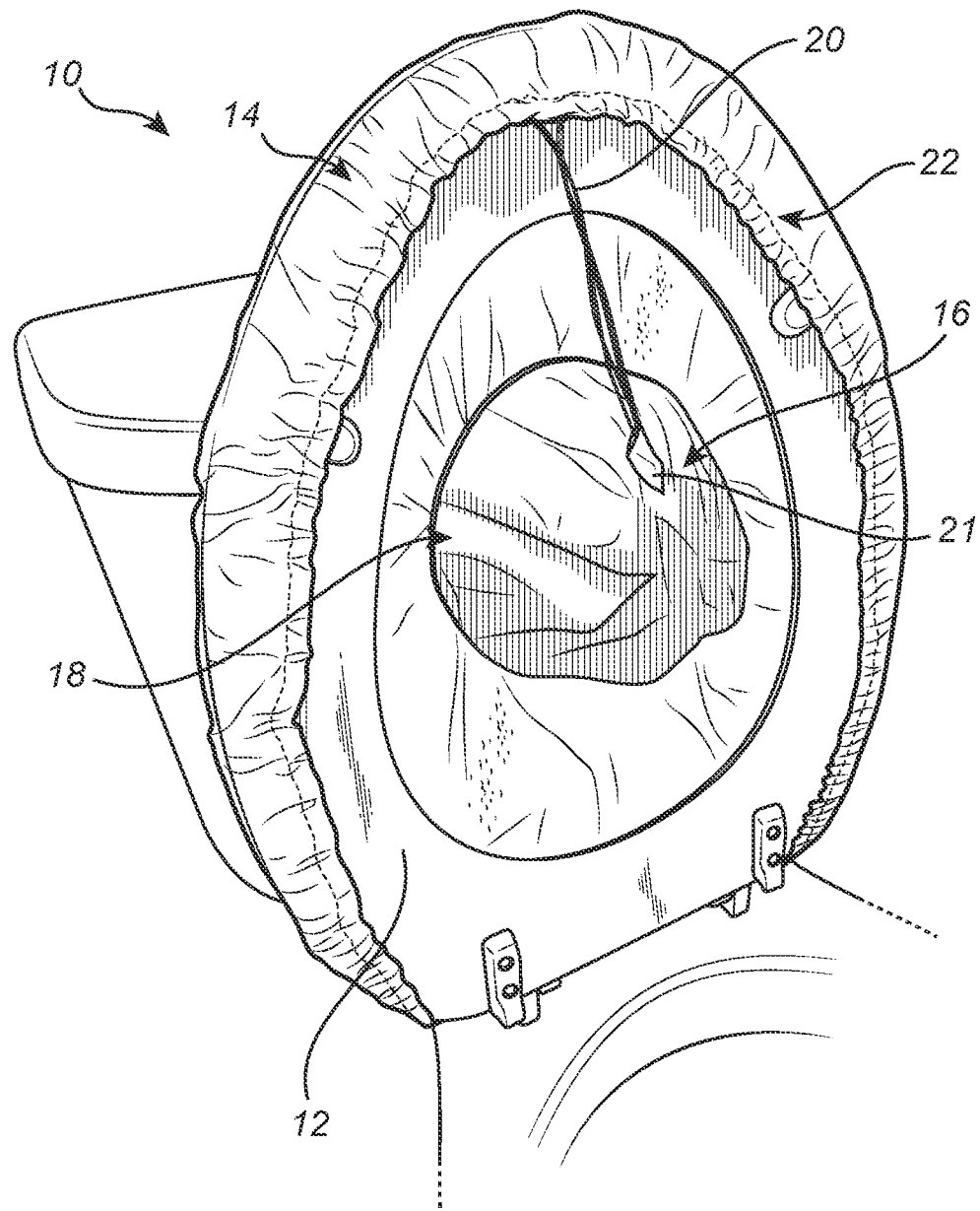
FIG. 2 is an isometric view of a non-limiting embodiment of the underside of the present invention.
Figure 3:
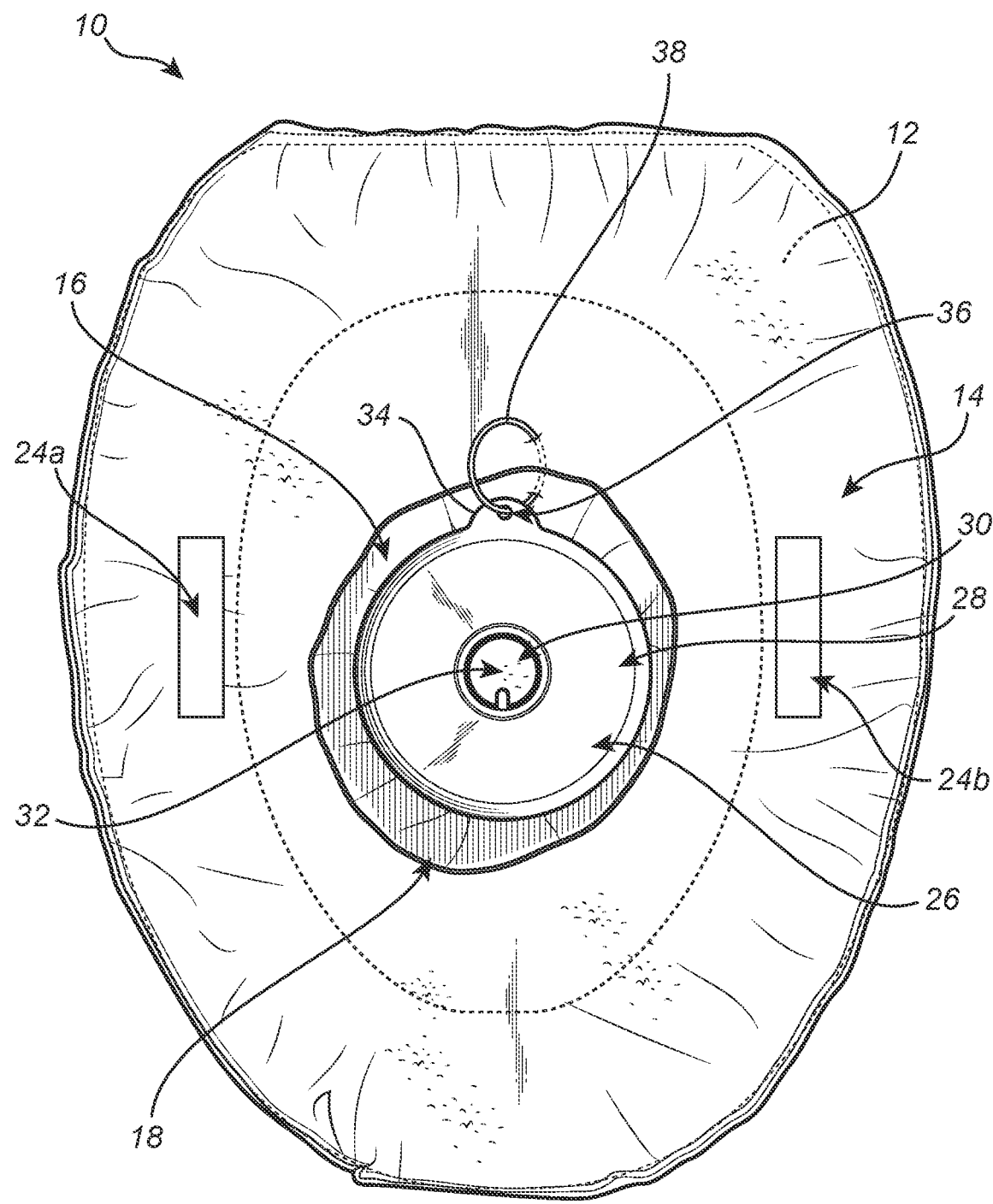
FIG. 3 is a top view of a non-limiting embodiment of the present invention including a specimen collector.

Referring now specifically to the drawings, a non-limiting embodiment of the toilet seat cover of the present invention is illustrated in FIGS. 1-3 and is shown generally at reference numeral 10. The toilet seat cover 10 is removably attachable to toilet seat 12. Toilet seat cover 10 is shown as it would be used on (attached to) toilet seat 12. The toilet seat cover 10 comprises a sheet 14 that is capable of covering the top of the toilet seat 12 and part of the opening of the toilet seat 12. Trap 16 attaches to sheet 14 along circumference 18. The material of trap 16 provides a shield between a user of the toilet seat cover 10 and the toilet bowl (not shown). The toilet seat cover sheet 14 is larger than the toilet seat 12. The toilet seat cover sheet 14 can be secured to the toilet seat 12 by drawstring 20. Handgrip 21 provides ready ease for pulling drawstring 20. As shown in FIG. 2, drawstring 20 can be housed in casing 22 to allow drawstring 20 to secure the toilet seat cover 10 to the toilet seat 12. As shown in FIG. 3, handles 24a and 24b can be used to remove the toilet seat cover 10 from the toilet seat 12 and allow the toilet seat cover 10 to fall into the toilet bowl (not shown).

FIG. 3 is a top view of a non-limiting embodiment of the toilet seat cover 10 with a specimen collector 26 secured within the trap 16. Specimen collector 26 is a circular apparatus with a solid section 28 sloping down toward specimen collection area 30. Specimen collection area 30 has a small opening partially blocked by filter 32 to allow urine to pass through the specimen collector 26 and the specimen (e.g., a kidney stone, feces, etc.) to remain on the specimen collector 26. Handle 34 has opening 36. Clip 38 is used to removably attach the specimen collector 26 to the toilet seat cover 10 by securing the handle 34 to the trap 16 and sheet 14.

The toilet seat cover comprises a sheet. The size of the sheet is slightly larger than a toilet seat. The shape of the sheet can be rectangle, round, or oval. Unlike conventional toilet seat cover, the opening in the sheet does not expose the toilet bowl water when the toilet seat cover is removably attached to a toilet seat.

The trap is centrally located on the sheet, attached to the sheet along circumference 18 which defines the opening in the sheet, and provides a barrier between the opening and the toilet bowl water. The trap is centrally located on the sheet such that the opening in the sheet is near the center of the toilet seat opening when the toilet seat cover is removably attached to the toilet. The shape of the trap is not particularly limiting. In some aspects, the trap is in the shape of a bowl, similar to a mask around the opening in the sheet. In some aspect, the trap is in the shape of an open cone. In some aspects, the trap is in the shape of an open cuboid. In some aspects, the trap is in a shape selected from the group consisting of a bowl, an open cone, an open cylinder, or an open cuboid. Unlike the sheet, the trap is expected to be assaulted with urine. To enhance integrity of the trap, in some aspects the bottom of the trap is made of thicker material than the sheet. In some aspects, a bottom section of the trap is made of a thicker material than the sheet. In some aspects, the whole trap is made of a thicker material than the sheet.

The toilet seat cover comprises a device capable of removably attaching the toilet seat cover to the toilet seat. The device can be as simple as one or more adhesive strip(s) on the bottom of the sheet to secure the sheet to the toilet seat. In some aspects, the device is one or more adhesive strip(s) on the bottom of the sheet. In some aspects, the one or more adhesive strip(s) is water-soluble. In some aspects, the device is located in a casing proximate an outer edge of the sheet. In some aspects, the device is a drawstring. When the toilet seat cover is placed on a toilet seat, and the drawstring is pulled, the edges of the sheet pull in and can be located under the toilet seat. The drawstring is not particularly elastic, and some of the drawstring hangs down from the toilet seat. In some aspects, a handgrip can be used to readily pull the drawstring. In some aspects, the device is located in a casing proximate an outer edge of the sheet, and the device is an elastic string. In this aspect, the elastic string is pulled out from the sheet outer edge as the toilet seat cover is being placed on the toilet seat. The elastic string is pulled down slightly under the toilet seat and let go such that the elastic string remains under the toilet seat until the toilet seat cover is removed. Removing the removably attachable toilet seat cover can be accomplished by pulling the edge of the sheet from under the toilet seat. In some aspects, the drawstring can be used to pull the toilet seat cover off the toilet seat. In some aspects, the toilet seat cover further comprises two handles located on the top of the sheet and on opposite sides of the trap. The two handles are useful in removing the toilet seat cover from the toilet seat while avoiding any contact between the user's hands and any toilet part. In some aspects, the toilet seat cover, removed from the toilet seat, can be dropped into the toilet bowl.

In some aspects, the toilet seat cover further comprises specimen collector capable of being removably attached to the trap and useful for collecting medical samples. How the specimen collector is removably attached to the trap is not particularly limiting. In some aspects, the specimen collector is simply supported by the bottom of the trap and/or the walls of the trap. In some aspects, the specimen collector is secured to the trap and/or the sheet using a clip or a tie. In some aspects, there are two small openings, one on the back of the trap and the other on the sheet, very close to the trap. In some aspects, a clip removably attaches to a hole in the specimen collector and the two small openings on the toilet seat cover to secure the specimen collector while a specimen is being collected. Once the specimen has been collected, the clip can be detached from the toilet seat cover and the specimen collector, now containing the specimen, can be removed from the toilet seat cover. In some aspects, the specimen collector is not flushable.

In some aspects, the toilet seat cover is flushable. In some aspects, the sheet and the trap are made from non-woven fabric. In some aspects, the sheet and the trap are made of PELLON water-soluble fabric. In some aspects the toilet seat cover consists of water-soluble material. In some aspects, the toilet seat cover consists of biodegradable materials. In some aspects, the toilet seat cover consists of water-soluble material and/or biodegradable material. In some aspects, the toilet seat cover is hypoallergenic.

In some aspects, a biodegradable décor is located on the top of the sheet. In some aspects, the décor is visible over the toilet seat when the toilet seat cover is removable attached to the toilet. In some aspects, the biodegradable décor is water-soluble.

The toilet seat cover provides a barrier between the user and the toilet seat. Some uses might also desire a barrier between the user and a toilet seat lid. In some aspects, the toilet seat cover further comprises a top cover. In some aspects, a bottom edge of the top cover is connected to a back edge of the sheet. In some aspects, the top cover is capable of covering an upright toilet bowl lid when the toilet seat cover is removably attached to the toilet seat.

According to another embodiment of the present invention, a toilet seat cover comprises a) a sheet capable of covering a toilet seat, b) a trap attached to the sheet and centrally located on the sheet, and c) a device capable of removably attaching the toilet seat cover to the toilet seat. The trap provides an opening in the sheet and a barrier between the opening and a toilet bowl water when the toilet seat cover is removably attached to the toilet seat. The toilet seat cover is water soluble and hypoallergenic. The sheet and the trap are made of non-woven fabric.

In some aspects, a bottom section of the trap is made of a thicker non-woven fabric than the sheet. In some aspects, the bottom of the trap is made with a thicker non-woven fabric than the sheet. In some aspects, at least a part of the trap is made with a thicker non-woven fabric than the sheet. In some aspects the trap is made with a thicker non-woven fabric than the sheet. One, non-limiting way to make the non-woven fabric thicker is to use stack two or more pieces of the non-woven fabric together.

The toilet seat cover comprises a device capable of removably attaching the toilet seat cover to the toilet seat. The device can be as simple as one or more adhesive strip(s) on the bottom of the sheet to secure the sheet to the toilet seat. In some aspects, the device is one or more adhesive strip(s) on the bottom of the sheet. In some aspects, the one or more adhesive strip(s) is water-soluble In some aspects, the device is located in a casing proximate an outer edge of the sheet. In some aspects, the device is a drawstring. When the toilet seat cover is placed on a toilet seat, and the drawstring is pulled, the edges of the sheet pull in and can be located under the toilet seat. The drawstring is not particularly elastic, and some of the drawstring hangs down from the toilet seat. In some aspects, a handgrip can be used to readily pull the drawstring. In some aspects, the drawstring and/or the handgrip are water-soluble. In some aspects, the device is located in a casing proximate an outer edge of the sheet, and the device is an elastic string. In some aspects, the elastic string is water soluble. In this aspect, the elastic string is pulled out from the sheet outer edge as the toilet seat cover is being placed on the toilet seat. The elastic string is pulled down slightly under the toilet seat and let go such that the elastic string remains under the toilet seat until the toilet seat cover is removed. Removing the removably attachable toilet seat cover can be accomplished by pulling the edge of the sheet from under the toilet seat. In some aspects, the drawstring can be used to pull the toilet seat cover off the toilet seat. In some aspects, the toilet seat cover further comprises two handles located on the top of the sheet and on opposite sides of the trap. The two handles are useful in removing the toilet seat cover from the toilet seat while avoiding any contact between the user's hands and any toilet part. In some aspects, the toilet seat cover, removed from the toilet seat, can be dropped into the toilet bowl.

In some aspects, the toilet seat cover further comprises specimen collector capable of being removably attached to the trap and useful for collecting medical samples. How the specimen collector is removably attached to the trap is not particularly limiting.

In some aspects, the specimen collector is simply supported by the bottom of the trap and/or the walls of the trap. In some aspects, the specimen collector is secured to the trap and/or the sheet using a clip or a tie. In some aspects, there are two small openings, one on the back of the trap and the other on the sheet, very close to the trap. In some aspects, a clip removably attaches to a hole in the specimen collector and the two small openings on the toilet seat cover to secure the specimen collector while a specimen is being collected. Once the specimen has been collected, the clip can be detached from the toilet seat cover and the specimen collector, with the specimen, can be removed from the toilet seat cover. In some aspects, the specimen collector is not flushable.

In some aspects, the sheet and the trap are made of PELLON water-soluble fabric. In some aspects, a biodegradable décor is located on the top of the sheet. In some aspects, the décor is visible over the toilet seat when the toilet seat cover is removable attached to the toilet.

According to yet another embodiment of the present invention, a toilet seat cover comprises a) a sheet capable of covering a toilet seat, b) a trap attached to the sheet and centrally located on the sheet, c) a device capable of removably attaching the toilet seat cover to the toilet seat, and d) an optional specimen collector capable of being removably attached to the trap and useful for collecting medical samples. The trap provides an opening in the sheet and a barrier between the opening and a toilet bowl water when the toilet seat cover is removably attached to the toilet seat. The trap is cylindrical or bowl shaped and capable of receiving the biological specimen collector, and the bottom of the trap comprises thicker fabric than the rest of the trap and/or the sheet. The device is located in a casing proximate an outer edge of the sheet, and the device is selected from the group consisting of a drawstring or an elastic string. The sheet, the trap, and the device are water soluble.

According to yet another embodiment of the present invention, a toilet seat cover comprises a) a sheet capable of covering a toilet seat, b) a trap attached to the sheet and centrally located on the sheet, c) a device capable of removably attaching the toilet seat cover to the toilet seat, and d) a specimen collector capable of being removably attached to the trap and useful for collecting medical samples. The trap provides an opening in the sheet and a barrier between the opening and a toilet bowl water when the toilet seat cover is removably attached to the toilet seat. The trap is cylindrical or bowl shaped and capable of receiving the biological specimen collector, and the bottom of the trap comprises thicker fabric than the rest of the trap and/or the sheet. The device is located in a casing proximate an outer edge of the sheet, and the device is selected from the group consisting of a drawstring or an elastic string. The sheet, the trap, and the device are water soluble.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A toilet seat cover comprising:
   a) a sheet capable of covering a toilet seat;
   b) a trap attached to the sheet and centrally located on the sheet; and
   c) a device capable of removably attaching the toilet seat cover to the toilet seat,
      wherein the sheet and trap are configured to cover an entirety of the toilet seat and a toilet bowl beneath the seat;
      wherein the trap is provided within an opening in the sheet and provides a barrier between the opening and toilet bowl water when the toilet seat cover is removably attached to the toilet seat,
      wherein the sheet and trap are made from a nonwoven, water-soluble, continuous fabric that provides a shield between a user of the toilet and the toilet bowl;
      wherein the trap is made of fabric that allows urine to pass through the fabric, and
      wherein the trap is attached to the sheet along a circumference of the opening.

2. The toilet seat cover of claim 1, wherein the trap is in a shape selected from the group consisting of a bowl, an open cone, an open cylinder, or an open cuboid.

3. The toilet seat cover of claim 1, wherein a bottom of the trap is made of thicker material than the sheet.

4. The toilet seat cover of claim 1, wherein the device is located in a casing proximate an outer edge of the sheet, and wherein the device is selected from the group consisting of a drawstring or an elastic string.

5. The toilet seat cover of claim 1, further comprising two handles located on the top of the sheet and on opposite sides of the trap, wherein the two handles are useful in removing the toilet seat cover from the toilet seat.

6. The toilet seat cover of claim 1, further comprising a specimen collector capable of being removably attached to the trap and useful for collecting medical samples.

7. The toilet seat cover of claim 6, wherein the specimen collector is secured to the trap and/or the sheet via a clip.

8. The toilet seat cover of claim 1, wherein the toilet seat cover consists of water-soluble material and/or biodegradable material.

9. The toilet seat cover of claim 1, wherein the toilet seat cover is hypoallergenic.

10. The toilet seat cover of claim 1, further comprising a top cover, wherein a bottom edge of the top cover is connected to a back edge of the sheet, and wherein the top cover is capable of covering an upright toilet bowl lid when the toilet seat cover is removably attached to the toilet seat.

11. A toilet seat cover comprising:
   a) a sheet capable of covering a toilet seat;
   b) a trap attached to the sheet and centrally located on the sheet; and
   c) a device capable of removably attaching the toilet seat cover to the toilet seat,
      wherein the sheet and trap are configured to cover an entirety of the toilet seat and a toilet bowl beneath the seat;
      wherein the trap is provided within an opening in the sheet and provides a barrier between the opening and toilet bowl water when the toilet seat cover is removably attached to the toilet seat,
      wherein the sheet and trap are made of a water-soluble, nonwoven, and continuous fabric that allows urine to pass through the fabric providing a shield between a user of the toilet and the toilet bowl;
      wherein the trap is attached to the sheet along a circumference of the opening and wherein the toilet seat cover is water soluble and hypoallergenic.

12. The toilet seat cover of claim 11, wherein a bottom section of the trap is made of a thicker amount of the non-woven fabric than the sheet.

13. The toilet seat cover of claim 11, wherein the device is located in a casing proximate an outer edge of the sheet, and wherein the device is selected from the group consisting of a drawstring or an elastic string.

14. The toilet seat cover of claim 11, further comprising two handles located on the top of the sheet and on opposite sides of the trap, wherein the two handles are useful in removing the toilet seat cover from the toilet seat.

15. The toilet seat cover of claim 11, further comprising a specimen collector capable of being removably attached to the trap and useful for collecting medical samples.

16. The toilet seat cover of claim 11, wherein the sheet and the trap are made of a water-soluble fabric.

17. A toilet seat cover comprising:
   a) a sheet capable of covering a toilet seat;
   b) a trap attached to the sheet and centrally located on the sheet;
   c) a device capable of removably attaching the toilet seat cover to the toilet seat; and
   d) a specimen collector removably attached to the trap, the specimen collector comprises a solid outer portion having an opening at a center thereof and a filter is provided at the center for collecting medical samples,
      wherein the sheet and trap are configured to cover an entirety of the toilet seat and a toilet bowl beneath the seat;
      wherein the trap is provided with an opening in the sheet and provides a barrier between the opening and toilet bowl water when the toilet seat cover is removably attached to the toilet seat,
      wherein the sheet and trap are made of a water-soluble, nonwoven, and continuous fabric that allows urine to pass through the fabric providing a shield between a user of the toilet and the toilet bowl,
      wherein the trap is attached to the sheet along a circumference of the opening wherein the trap is cylindrical or bowl shaped and capable of supporting the biological specimen collector,
      wherein a bottom of the trap comprises thicker fabric than the rest of the trap and/or the sheet,
      wherein the device is located in a casing proximate an outer edge of the sheet,
      wherein the device is water soluble.

18. The toilet seat cover of claim 1, further comprising a casing extending around an outer periphery of the sheet and the device capable of removably attaching the toilet seat cover to the toilet seat is a drawstring secured in the casing.

* * * * *